US012557966B2

(12) United States Patent
Yamamura

(10) Patent No.: US 12,557,966 B2
(45) Date of Patent: Feb. 24, 2026

(54) SIGNAL PROCESSING DEVICE, ENDOSCOPE SYSTEM, AND SIGNAL PROCESSING METHOD

(71) Applicant: OLYMPUS CORPORATION, Hachioji (JP)

(72) Inventor: Daiki Yamamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 624 days.

(21) Appl. No.: 17/902,268

(22) Filed: Sep. 2, 2022

(65) Prior Publication Data

US 2022/0409009 A1 Dec. 29, 2022

Related U.S. Application Data

(63) Continuation of application No. PCT/JP2020/009791, filed on Mar. 6, 2020.

(51) Int. Cl.
*A61B 1/00* (2006.01)
*A61B 1/06* (2006.01)

(52) U.S. Cl.
CPC ........ *A61B 1/00006* (2013.01); *A61B 1/0655* (2022.02)

(58) Field of Classification Search
CPC .............. A61B 1/00006; A61B 1/0655; A61B 1/000095; A61B 1/045; H04N 23/60; H04N 23/665
See application file for complete search history.

(56) References Cited

U.S. PATENT DOCUMENTS 2,072,528 A * 3/1937 Mclean .................... H04N 3/12
                                                     348/222.1
4,298,260 A * 11/1981 Takayama ............ A61B 1/0669
                                                     396/17
4,931,867 A * 6/1990 Kikuchi ................. H04N 23/84
                                                     348/E5.025

(Continued)

FOREIGN PATENT DOCUMENTS

JP        5-94226 A      4/1993
JP     2003-234652 A     8/2003

(Continued)

OTHER PUBLICATIONS

International Search Report dated Jun. 9, 2020, issued in counterpart International Application No. PCT/JP2020/009791. (2 pages).

*Primary Examiner* — Anh Tuan T Nguyen
*Assistant Examiner* — Jae Woo
(74) *Attorney, Agent, or Firm* — WHDA, LLP

(57) ABSTRACT

A signal processing device includes a processor including at least one or more pieces of hardware. The processor is configured to: when a first synchronization signal from a first synchronization signal generation circuit, the first synchronization signal generation circuit receiving a first clock signal and outputting the first synchronization signal, and a second synchronization signal output from a second synchronization signal generation circuit are not synchronized, reset the first synchronization signal generation circuit, and in a period in which the first synchronization signal generation circuit is reset, set a frequency of the first clock signal to be higher than a frequency in another period.

18 Claims, 7 Drawing Sheets

(56) References Cited

U.S. PATENT DOCUMENTS

| | | | | |
|---|---|---|---|---|
| 5,225,958 | A * | 7/1993 | Nakamura | A61B 1/121 |
| | | | | 361/111 |
| 5,465,147 | A * | 11/1995 | Swanson | A61B 1/00183 |
| | | | | 356/497 |
| 7,355,625 | B1 * | 4/2008 | Mochida | H04N 23/60 |
| | | | | 348/E7.087 |
| 9,319,603 | B2 * | 4/2016 | Dai | H04N 25/70 |
| 2003/0025789 | A1 * | 2/2003 | Saito | H04N 21/47 |
| | | | | 348/E9.037 |
| 2006/0197997 | A1 * | 9/2006 | Oshida | H04N 1/12 |
| | | | | 358/498 |
| 2007/0070195 | A1 * | 3/2007 | Abe | A61B 1/045 |
| | | | | 348/74 |
| 2008/0002036 | A1 * | 1/2008 | Ohwa | H04N 23/667 |
| | | | | 348/222.1 |
| 2010/0066846 | A1 * | 3/2010 | Sarwari | H04N 23/951 |
| | | | | 348/E5.024 |
| 2012/0016202 | A1 * | 1/2012 | Baum | H04N 23/66 |
| | | | | 600/182 |
| 2012/0249763 | A1 * | 10/2012 | Hashimoto | A61B 1/00006 |
| | | | | 348/E7.087 |
| 2012/0307029 | A1 * | 12/2012 | Nambakam | A61B 1/00016 |
| | | | | 348/E5.009 |
| 2013/0271586 | A1 * | 10/2013 | Komine | A61B 1/00006 |
| | | | | 348/65 |
| 2014/0125839 | A1 * | 5/2014 | Shiohara | H04N 23/73 |
| | | | | 348/229.1 |
| 2017/0288684 | A1 * | 10/2017 | Ogihara | H03L 7/095 |
| 2018/0042450 | A1 * | 2/2018 | Saito | G02B 23/24 |
| 2018/0218482 | A1 * | 8/2018 | Ganesan | G06T 7/10 |
| 2018/0332249 | A1 * | 11/2018 | Ogasawara | A61B 1/00114 |
| 2020/0214540 | A1 * | 7/2020 | Tanaka | H04N 23/555 |
| 2020/0396378 | A1 * | 12/2020 | Jeong | H03L 7/08 |
| 2021/0044770 | A1 * | 2/2021 | Saito | H03L 7/104 |
| 2021/0132362 | A1 * | 5/2021 | Yamazaki | A61B 1/00006 |
| 2021/0145250 | A1 * | 5/2021 | Kato | H04N 23/555 |
| 2021/0177241 | A1 * | 6/2021 | Tanaka | A61B 1/00013 |
| 2021/0195098 | A1 * | 6/2021 | Ito | H04N 23/63 |
| 2022/0211253 | A1 * | 7/2022 | Kato | A61B 1/045 |
| 2022/0217249 | A1 * | 7/2022 | Koyama | H04N 23/66 |
| 2022/0409031 | A1 * | 12/2022 | Yamamura | H04N 23/665 |

FOREIGN PATENT DOCUMENTS

| | | | |
|---|---|---|---|
| JP | 2019-28651 | A | 2/2019 |
| WO | 2017/002437 | A1 | 1/2017 |

* cited by examiner

SIGNAL PROCESSING DEVICE, ENDOSCOPE SYSTEM, AND SIGNAL PROCESSING METHOD

CROSS-REFERENCE TO RELATED APPLICATION

This application is a continuation of International Application No. PCT/JP2020/009791, filed on Mar. 6, 2020, the entire contents of which are incorporated herein by reference.

BACKGROUND

1. Technical Field

The present disclosure relates to a signal processing device, an endoscope system, and a signal processing method.

2. Related Art

In the related art, there is known an endoscope system including an endoscope in which an imager is provided at a distal end and which is inserted into a subject, and a processor that processes an image signal from the imager.

In such an endoscope system, the processor outputs, to the imager, a clock signal for operating the imager and a synchronization signal (hereinafter, described as a second synchronization signal.) indicating timing at which an image signal is acquired for each frame from the imager. Then, the imager operates according to the clock signal and outputs the image signal to the processor at timing based on the second synchronization signal.

Meanwhile, in recent years, in order to downsize an imager, a configuration has been proposed in which a function of transmitting and receiving a synchronization signal is removed from a function of the imager (see, for example, U.S. Pat. No. 9,319,603 B2).

In the technique described in U.S. Pat. No. 9,319,603 B2, in order to generate a synchronization signal from an image signal in an imager, a change in a voltage level is provided in the image signal. Then, in the technology, a synchronization signal generation unit that generates a first synchronization signal indicating timing at which the image signal is transmitted for each frame based on the change in the voltage level is provided, and the first synchronization signal is output from the synchronization signal generation unit to the processor.

SUMMARY

In some embodiments, a signal processing device includes a processor comprising at least one or more pieces of hardware, the processor being configured to: when a first synchronization signal from a first synchronization signal generation circuit, the first synchronization signal generation circuit receiving a first clock signal and outputting the first synchronization signal, and a second synchronization signal output from a second synchronization signal generation circuit are not synchronized, reset the first synchronization signal generation circuit, and in a period in which the first synchronization signal generation circuit is reset, set a frequency of the first clock signal to be higher than a frequency in another period.

In some embodiments, an endoscope system includes: an endoscope configured to be inserted into a subject; and a processor comprising at least one or more pieces of hardware, the processor being configured to: when a first synchronization signal from a first synchronization signal generation circuit, the first synchronization signal generation circuit receiving a clock signal and outputting the first synchronization signal, and a second synchronization signal output from a second synchronization signal generation circuit are not synchronized, reset the first synchronization signal generation circuit, and in a period in which the first synchronization signal generation circuit is reset, set a frequency of the clock signal to be higher than a frequency in another period.

In some embodiments, provided is a signal processing method executed by a processor including at least one or more pieces of hardware. The signal processing method includes: when a first synchronization signal from a first synchronization signal generation circuit, the first synchronization signal generation circuit receiving a clock signal and outputting the first synchronization signal, and a second synchronization signal output from a second synchronization signal generation circuit are not synchronized, resetting the first synchronization signal generation circuit; and in a period in which the first synchronization signal generation circuit is reset, setting a frequency of the clock signal to be higher than a frequency in another period.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
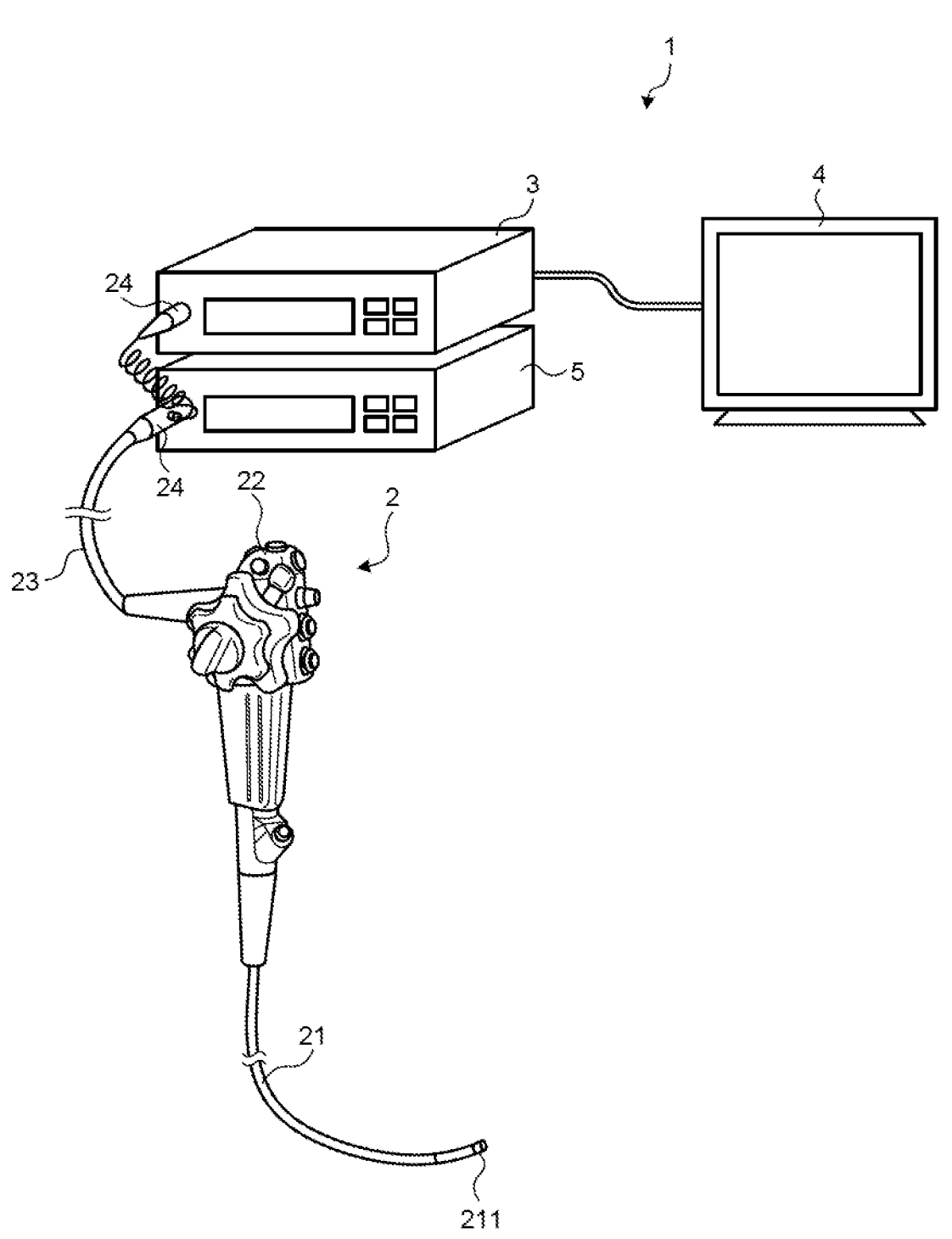
FIG. 1 is a diagram illustrating a configuration of an endoscope system according to a first embodiment.

Hereinafter, modes for carrying out the disclosure (embodiments) will be described with reference to the drawings. Note that the disclosure is not limited by the embodiments described below. Further, in the description of the drawings, the same parts will be described with the same reference numerals.

First Embodiment

Configuration of Endoscope System

FIG. 1 is a diagram illustrating a configuration of an endoscope system 1 according to the first embodiment.

The endoscope system 1 is a system that is used, for example, in a medical field and observes the inside of a subject (inside of a living body). As illustrated in FIG. 1, the endoscope system 1 includes an endoscope 2, a second synchronization signal generation circuit 3, a display device 4, and a light source device 5.

The endoscope 2 is partially inserted into the living body and captures a subject image reflected from the inside of the living body, and outputs an image signal generated by the imaging. As illustrated in FIG. 1, the endoscope 2 includes an insertion unit 21, an operating unit 22, a universal cord 23, and a connector unit 24.

The insertion unit 21 is a portion at least part of which has flexibility and that is inserted into a living body. In the insertion unit 21, an imager 6 (see FIG. 2) is provided at a distal end portion 211 (FIG. 1).

Note that a detailed configuration of the imager 6 will be described in "Configuration of main part of endoscope system" described later.

The operating unit 22 is connected to a proximal end portion of the insertion unit 21. Then, the operating unit 22 receives various operations of the endoscope 2.

The universal cord 23 is a cord extending from the operating unit 22 in a direction different from the extending direction of the insertion unit 21 and provided with a cable for transmitting the above-described image signal and the like, an optical fiber for guiding illumination light emitted from the light source device 5, and the like.

The connector unit 24 is provided at an end portion of the universal cord 23, and is detachably connected to the second synchronization signal generation circuit 3 and the light source device 5. In the first embodiment, a first synchronization signal generation circuit 7 (see FIG. 2) and a signal processing device 8 (see FIG. 2) are provided in the connector unit 24.

Note that detailed configurations of the first synchronization signal generation circuit 7 and the signal processing device 8 will be described in "Configuration of main part of endoscope system" described later.

The second synchronization signal generation circuit 3 integrally controls the entire operation of the endoscope system 1. For example, the second synchronization signal generation circuit 3 performs various types of image processes on the image signal output from the imager 6 and having passed through the insertion unit 21, the operating unit 22, the universal cord 23, and the connector unit 24.

Note that a detailed configuration of the second synchronization signal generation circuit 3 will be described in "Configuration of main part of endoscope system" described later.

The display device 4 is a liquid crystal display (LCD), an electro luminescence (EL) display, or the like, and displays an image or the like based on an image signal subjected to image processing by the second synchronization signal generation circuit 3.

The light source device 5 corresponds to a light source. The light source device 5 includes, for example, a halogen lamp, a white light emitting diode (LED), and the like, and emits illumination light. Then, the illumination light emitted from the light source device 5 passes through the connector unit 24, the universal cord 23, the operating unit 22, and the insertion unit 21, and then is emitted from the distal end portion 211 of the insertion unit 21 toward the inside of the living body.

Configuration of Main Part of Endoscope System

Next, configurations of the imager 6, the first synchronization signal generation circuit 7, the signal processing device 8, and the second synchronization signal generation circuit 3 which are main parts of the endoscope system 1 will be described.

Figure 2:
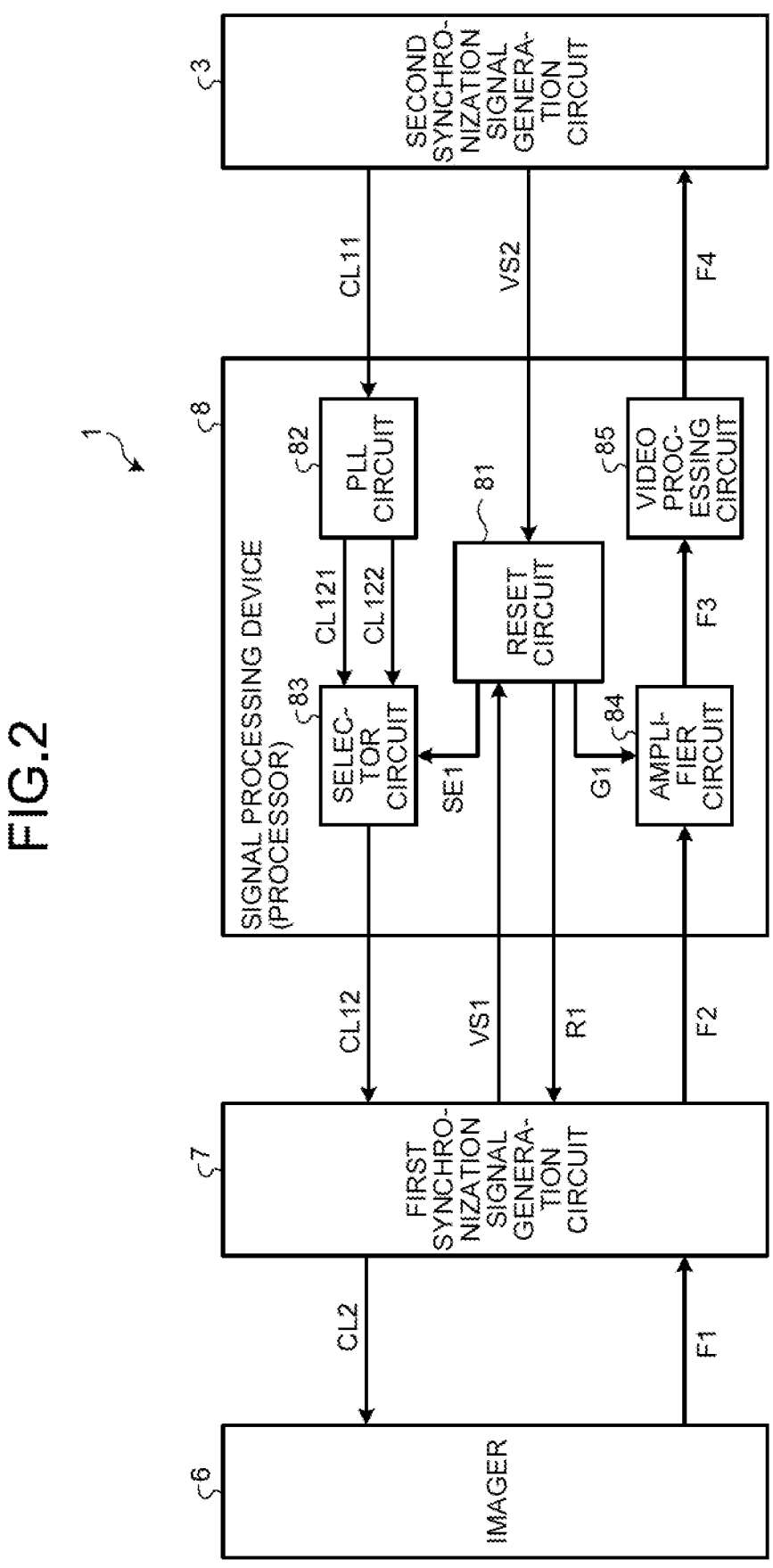
FIG. 2 is a block diagram illustrating a configuration of a main part of the endoscope system.

FIG. 2 is a block diagram illustrating a configuration of a main part of the endoscope system 1.

The imager 6 operates in accordance with a clock signal CL2 (FIG. 2). The clock signal CL2 is output from the first synchronization signal generation circuit 7, and is input to the imager 6 via the universal cord 23, the operating unit 22, and the insertion unit 21. Furthermore, the imager 6 captures an image of illumination light (subject image) emitted from the distal end portion 211 of the insertion unit 21 and reflected from the inside of the living body. Then, the imager 6 outputs an image signal F1 (FIG. 2) obtained by the imaging. Here, the imager 6 provides a change in a voltage level to the image signal F1 in order to cause the first synchronization signal generation circuit 7 to generate a synchronization signal VS1 (FIG. 2) from the image signal F1, for example, as in the technology described in U.S. Pat. No. 9,319,603 B2.

The imager 6 described above includes a charge coupled device (CCD), a complementary metal oxide semiconductor (CMOS), or the like that receives a subject image and converts the subject image into an electrical signal (analog signal).

The first synchronization signal generation circuit 7 includes an analog front end (AFE). In addition, the first synchronization signal generation circuit 7 includes a circuit that converts an analog signal into a digital signal (A/D conversion). Furthermore, the first synchronization signal generation circuit 7 generates the clock signal CL2 based on a clock signal CL12 (FIG. 2) input from the signal processing device 8. Then, the first synchronization signal generation circuit 7 outputs the clock signal CL2 to the imager 6. Furthermore, the image signal F1 output from the imager 6 and having passed through the insertion unit 21, the operating unit 22, and the universal cord 23 is input to the first synchronization signal generation circuit 7. Then, the first synchronization signal generation circuit 7 performs a predetermined signal process (for example, A/D conversion or the like) on the image signal F1 to generate an image signal F2 (FIG. 2). Further, the first synchronization signal generation circuit 7 generates the synchronization signal VS1 (FIG. 2) indicating timing at which the image signal F1 is transmitted for each frame based on a change in the voltage level of the input image signal F1, for example, as in the technique described in U.S. Pat. No. 9,319,603 B2. The synchronization signal VS1 corresponds to a first synchronization signal.

The signal processing device 8 includes a processor including at least one or more pieces of hardware such as a field programmable gate array (FPGA). As illustrated in FIG. 2, the signal processing device 8 includes a reset circuit 81, a phase locked loop (PLL) circuit 82, a selector circuit 83, an amplifier circuit 84, and a video processing circuit 85.

The reset circuit 81 determines whether the synchronization signal VS1 output from the first synchronization signal generation circuit 7 and the synchronization signal VS2 generated by the second synchronization signal generation circuit 3 are not synchronized. For example, when the pulse based on the synchronization signal VS1 and the pulse based on the synchronization signal VS2 rise at different times, the reset circuit 81 determines that the synchronization signal VS1 and the synchronization signal VS2 are not synchronized. When determining that the synchronization signal VS1 and the synchronization signal VS2 are not synchronized, the reset circuit 81 outputs a high-level reset signal R1 (FIG. 2) to the first synchronization signal generation circuit 7 during a certain period from a time point at which the pulse based on the synchronization signal VS2 first rises after the determination. In a period other than this period, the reset circuit 81 outputs a low-level reset signal R1 to the first synchronization signal generation circuit 7. When the high-level reset signal R1 is output to the first synchronization signal generation circuit 7, the first synchronization signal generation circuit 7 and the imager 6 start resetting. In addition, in a case where it is determined that the synchronization signal VS1 and the synchronization signal VS2 are not synchronized, the reset circuit 81 outputs a high-level select signal SE1 (FIG. 2) to the selector circuit 83 during a period from a time point at which the pulse based on the synchronization signal VS2 first rises after the determination until it is determined that the synchronization is established. In a period other than this period, the reset circuit 81 outputs a low-level select signal SE1 to the selector circuit 83. Further, when determining that the synchronization signal VS1 and the synchronization signal VS2 are not synchronized, the reset circuit 81 outputs a high-level gain signal G1 (FIG. 2) to the amplifier circuit 84 during a period from a time point at which the pulse based on the synchronization signal VS2 first rises after the determination until the image signal F1 for one frame is output from the imager 6 after the first synchronization signal generation circuit 7 is reset. In a period other than this period, the reset circuit 81 outputs a low-level gain signal G1 to the amplifier circuit 84.

The PLL circuit 82 is a frequency synthesizer, and generates the clock signal CL121 (FIG. 2) and the clock signal CL122 (FIG. 2) based on the clock signal CL11 (FIG. 2) output from the second synchronization signal generation circuit 3. Here, the clock signal CL121 is a clock signal having a higher frequency than the clock signal CL122. Then, the PLL circuit 82 outputs the clock signal CL121 and the clock signal CL122 to the selector circuit 83.

The selector circuit 83 is provided on a line between the second synchronization signal generation circuit 3 and the first synchronization signal generation circuit 7, and a clock signal is transmitted on the line. In addition, the selector circuit 83 selects one clock signal of the clock signal CL121 and the clock signal CL122 output from the PLL circuit 82. Specifically, the selector circuit 83 selects the clock signal CL122 having a low frequency during a period in which it receives a low-level select signal SE1 from the reset circuit 81. Then, the selector circuit 83 outputs the clock signal CL122 as a clock signal CL12 to the first synchronization signal generation circuit 7. On the other hand, the selector circuit 83 selects the clock signal CL121 having a high frequency during a period in which it receives a high-level select signal SE1 from the reset circuit 81. Then, the selector circuit 83 outputs the clock signal CL121 as the clock signal CL12 to the first synchronization signal generation circuit 7.

The amplifier circuit 84 is provided on a line between the first synchronization signal generation circuit 7 and the second synchronization signal generation circuit 3, and an image signal is transmitted on the line. Further, the amplifier circuit 84 adjusts the brightness of the image based on the image signal F2 by multiplying the pixel value of each pixel in the image signal F2 output from the first synchronization signal generation circuit 7 by the gain. Specifically, the amplifier circuit 84 generates the image signal F3 by multiplying the pixel value of each pixel in the image signal F2 by the first gain during a period in which it receives the low-level gain signal G1 from the reset circuit 81. On the other hand, the amplifier circuit 84 generates the image signal F3 by multiplying the pixel value of each pixel in the image signal F2 by a second gain larger than the first gain during a period in which it receives the high-level gain signal G1 from the reset circuit 81.

The video processing circuit 85 performs various types of image processes on the image signal F3 output from the amplifier circuit 84 to generate an image signal F4.

The second synchronization signal generation circuit 3 includes a central processing unit (CPU), an FPGA, and the like. The second synchronization signal generation circuit 3 generates the clock signal CL11 and the synchronization signal VS2 (FIG. 2) indicating the timing at which the image signal F4 is acquired for each frame to output the signals to the signal processing device 8 (the PLL circuit 82 and the reset circuit 81). In addition, the second synchronization signal generation circuit 3 performs various types of image processes on the image signal F4 output from the signal processing device 8 (video processing circuit 85). Then, the image based on the image signal after the execution of the various types of image processes is displayed on the display device 4.

Note that each of the clock signal CL11, the clock signal CL121, the clock signal CL122, and the clock signal CL12 described above correspond to a clock signal. The synchronization signal VS2 corresponds to a second synchronization signal.

Operation of Endoscope System

Next, an operation of the endoscope system 1 will be described. Note that operations of the imager 6, the first synchronization signal generation circuit 7, the signal processing device 8, and the second synchronization signal generation circuit 3, which are main parts of the endoscope system 1, will be mainly described below.

Figure 3:
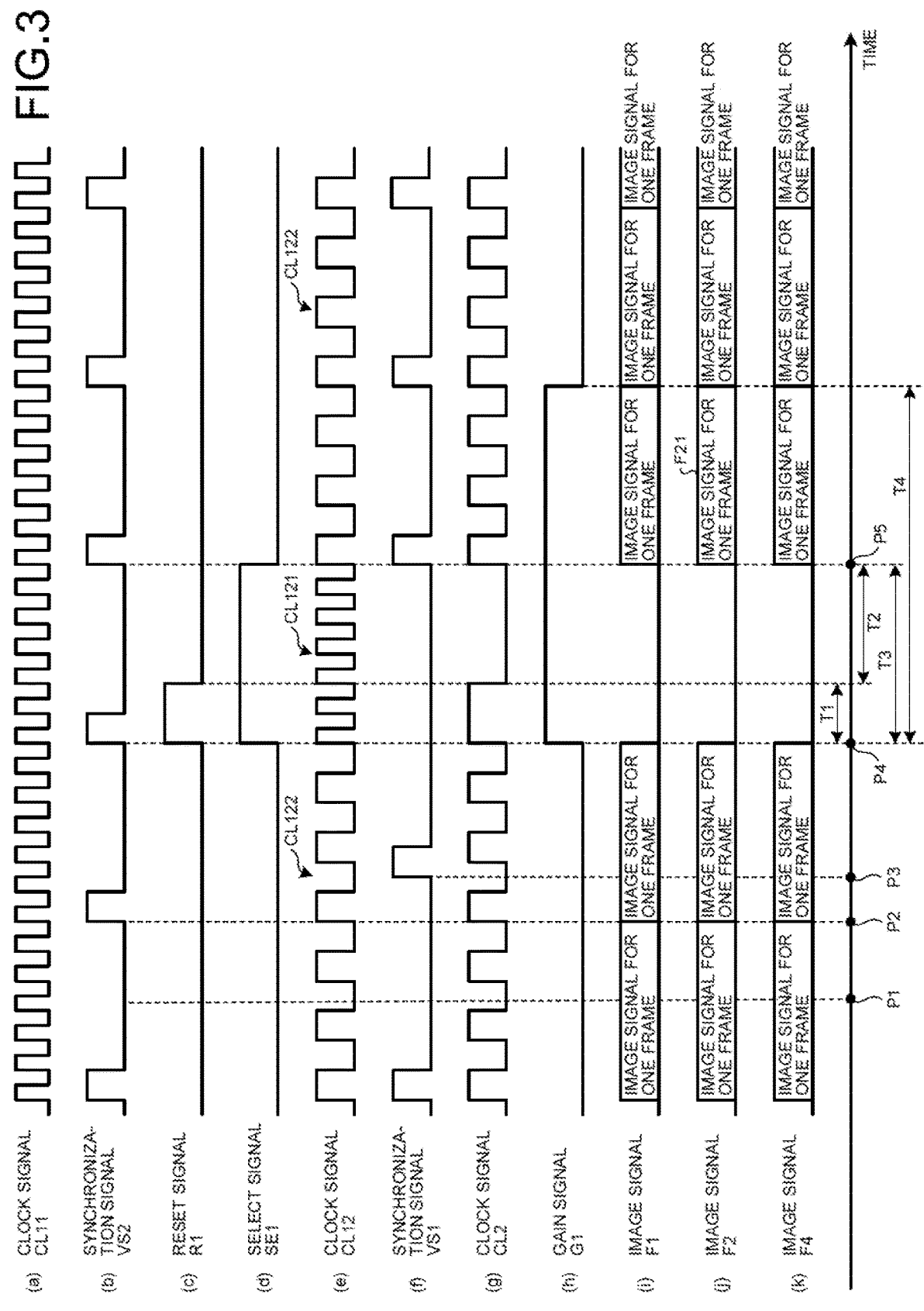
FIG. 3 is a time chart illustrating an operation of the endoscope system.

FIG. 3 is a time chart illustrating an operation of the endoscope system 1. Specifically, (a) to (k) in FIG. 3 illustrate the clock signal CL11, the synchronization signal VS2, the reset signal R1, the select signal SE1, the clock signal CL12, the synchronization signal VS1, the clock signal CL2, the gain signal G1, the image signal F1, the image signal F2, and the image signal F4, respectively.

Hereinafter, it is assumed that a treatment instrument such as an electric scalpel or a snare is used at high output at time P1 (FIG. 3), and the clock signal CL2 or the image signal F1 is affected by disturbance from the treatment instrument.

Here, the first synchronization signal generation circuit 7 detects a change in the voltage level of the image signal F1, thereby estimating which data of the image signal F1 for one frame is transmitted from the imager 6. Then, when the first synchronization signal generation circuit 7 estimates that the image signal F1 for one frame has been transmitted based on the change in the voltage level, the first synchronization signal generation circuit 7 starts a pulse based on the synchronization signal VS1. In the case described above, since the clock signal CL2 and the image signal F1 are affected by disturbance, a change other than the change in the voltage level generated by the imager 6 occurs in the image signal F1. Then, since the first synchronization signal generation circuit 7 detects a change other than the change in the voltage level generated by the imager 6, erroneous estimation is made. Therefore, the pulse based on the synchronization signal VS1 rises at time P3 (FIG. 3) shifted from time P2 (FIG. 3) at which the pulse based on the synchronization signal VS2 first rises after time P1 ((f) in FIG. 3). That is, the reset circuit 81 determines that the synchronization signal VS1 and the synchronization signal VS2 are not synchronized at time P2.

Then, the reset circuit 81 outputs the high-level reset signal R1 to the first synchronization signal generation circuit 7 during a certain period T1 from time P4 at which the pulse based on the synchronization signal VS2 first rises after time P2 ((c) in FIG. 3). As a result, the first synchronization signal generation circuit 7 and the imager 6 start resetting. The period T1 is a period from when the imager 6 starts resetting to when the resetting is completed. Here, in FIG. 3, a period T2 is a period in which charges are accumulated after the imager 6 is reset. In addition, the period T3 is a period from when the first synchronization signal generation circuit 7 starts resetting to when the resetting is completed. In the first embodiment, the period T3 is a vertical synchronization period (a period between adjacent pulses) based on the synchronization signal VS2. That is, the synchronization signal VS1 and the synchronization signal VS2 can be synchronized at time P5 when the pulse based on the synchronization signal VS2 first rises after time P4.

Further, the reset circuit 81 outputs the high-level select signal SE1 to the selector circuit 83 during a period T3 from time P4 until it is determined that the synchronization signal VS1 and the synchronization signal VS2 are synchronized ((d) in FIG. 3). As a result, the selector circuit 83 selects the clock signal CL121 having a high frequency from the clock signal CL121 and the clock signal CL122 output from the PLL circuit 82. Then, the selector circuit 83 outputs the clock signal CL121 as the clock signal CL12 to the first synchronization signal generation circuit 7 ((e) in FIG. 3). That is, the selector circuit 83 sets the frequency of the clock signal CL12 in the period T3 in which the first synchronization signal generation circuit 7 is reset to be higher than that in another period.

Furthermore, the reset circuit 81 outputs a high-level gain signal G1 to the amplifier circuit 84 during a period T4 from time P4 until the image signal F1 for one frame is output from the imager 6 after the first synchronization signal generation circuit 7 is reset ((h) in FIG. 3). As a result, during the period T4, the amplifier circuit 84 multiplies the pixel value of each pixel in the image signal F21 (F2) for one frame input from the first synchronization signal generation circuit 7 by the second gain larger than the first gain.

That is, the amplifier circuit 84 brightens the image based on the image signal F21 for one frame input during the period T4.

According to the first embodiment described above, the following effects are obtained.

Figure 4:
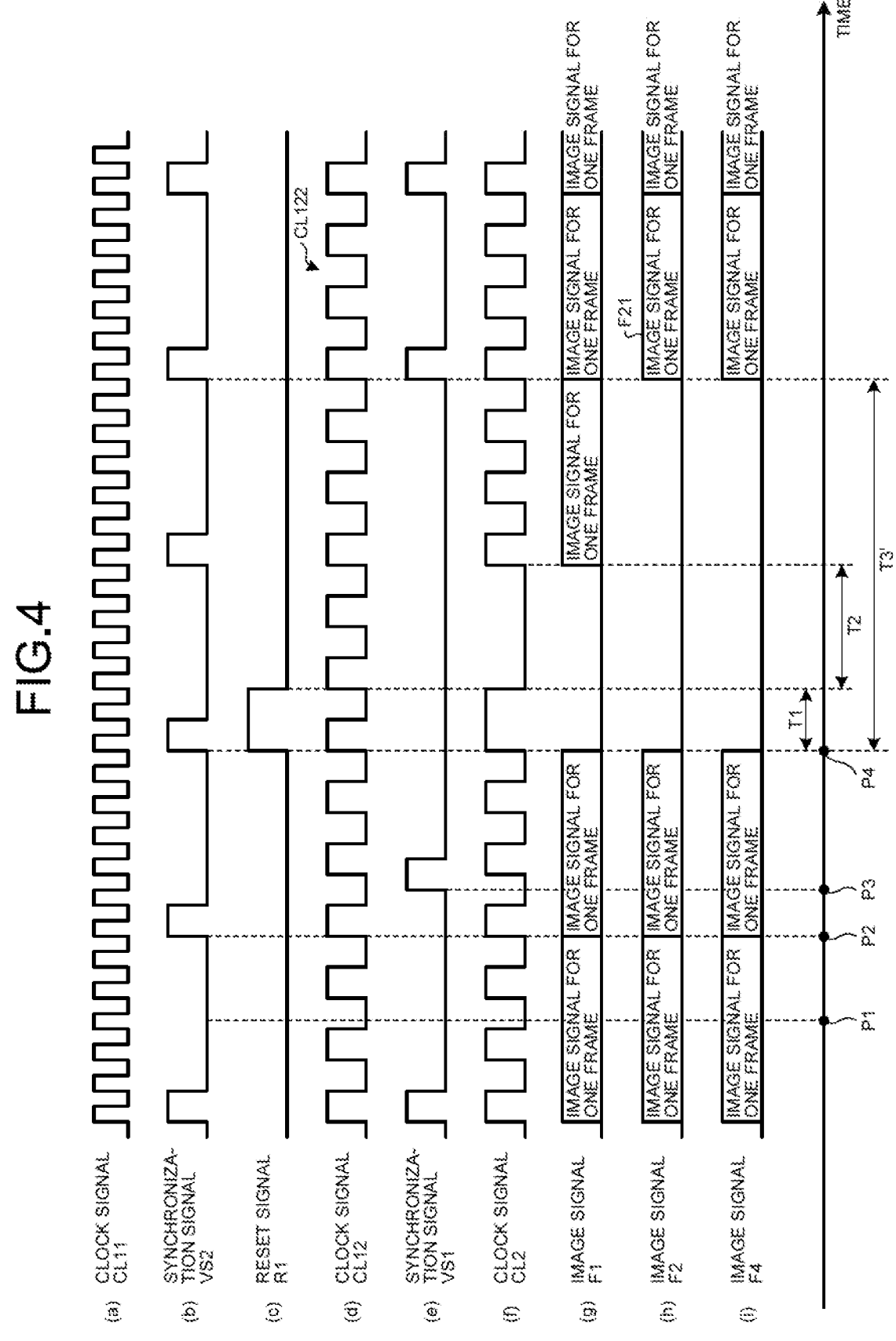
FIG. 4 is a view for describing effects of the first embodiment.

FIG. 4 is a diagram illustrating effects of the first embodiment. Note that FIG. 4 is a time chart corresponding to that in FIG. 3, and illustrates a case where the clock signal CL122, as the clock signal CL12, having a low frequency is input to the first synchronization signal generation circuit 7 even in the period T3' in which the first synchronization signal generation circuit 7 is reset as in another period. Specifically, (a) to (i) in FIG. 4 illustrate the clock signal CL11, the synchronization signal VS2, the reset signal R1, the clock signal CL12, the synchronization signal VS1, the clock signal CL2, the image signal F1, the image signal F2, and the image signal F4, respectively.

Meanwhile, as described above, the first synchronization signal generation circuit 7 estimates which data of the image signal F1 for one frame is transmitted from the imager 6 based on only the change in the voltage level of the image signal F1. Therefore, after the synchronization deviation between the synchronization signal VS1 and the synchronization signal VS2 occurs due to the influence of the disturbance, the synchronization deviation is not eliminated by the elapse of time. That is, in order to eliminate the synchronization deviation, it is necessary to reset the first synchronization signal generation circuit 7 and the imager 6.

The signal processing device 8 according to the first embodiment resets the first synchronization signal generation circuit 7 when the synchronization deviation occurs. Therefore, the synchronization deviation can be eliminated. That is, an image based on the image signal F1 generated by the imager 6 can be appropriately displayed.

Here, as illustrated in FIG. 4, it is assumed that the clock signal CL122 having a low frequency as the clock signal CL12 is input to the first synchronization signal generation circuit 7 also during the period T3' in which the first synchronization signal generation circuit 7 is reset, as in another period. In this case, since the operation of the first synchronization signal generation circuit 7 cannot be accelerated by the clock signal CL12, the period T3' from the start of the reset by the first synchronization signal generation circuit 7 to the completion of the reset is long. For example, the period T3' is twice a vertical synchronization period (a period between adjacent pulses) based on the synchronization signal VS2. Here, during the period T3', the image signal F2 is not output from the first synchronization signal generation circuit 7. That is, as the period T3' is longer, the period during which no image is displayed on the display device 4 is longer.

On the other hand, the signal processing device 8 according to the first embodiment includes the selector circuit 83 that sets the frequency of the clock signal CL12 in the period T3 in which the first synchronization signal generation circuit 7 is reset to be higher than that in another period. Therefore, the operation of the first synchronization signal generation circuit 7 can be accelerated by the clock signal CL12, and the period T3 from the start of the reset by the first synchronization signal generation circuit 7 to the completion of the reset can be shortened. For example, the period T3 is a vertical synchronization period (a period between adjacent pulses) based on the synchronization signal VS2. That is, since the period T3 can be shortened, the period during which no image is displayed on the display device 4 can be shortened.

Meanwhile, the image signal F2 for one frame is an image signal generated by accumulating charges during a vertical synchronization period (a period between adjacent pulses) based on the synchronization signal VS2. On the other hand, the image signal F21 for one frame input to the signal processing device 8 during the period T4 is an image signal generated by accumulating charges during the short period T2 with respect to the image signal F2 for another one frame. Therefore, the image based on the image signal F21 has relatively dark brightness.

Here, the signal processing device 8 according to the first embodiment includes the amplifier circuit 84 that makes an image based on the image signal F21 for one frame input during the period T4 brighter than an image based on the image signal F2 for another frame. Therefore, the image based on the image signal F21 can be brightened, and an appropriate image can be displayed.

In addition, the imager 6 has a configuration in which a function of transmitting and receiving a synchronization signal is removed. Therefore, the imager 6 can be downsized, whereby the diameter of the insertion unit 21 provided with the imager 6 can be reduced.

Second Embodiment

Next, the second embodiment will be described.

In the following description, the same reference numerals are given to the same configurations as those of the above-described first embodiment, and detailed configurations thereof are omitted or simplified.

Figure 5:
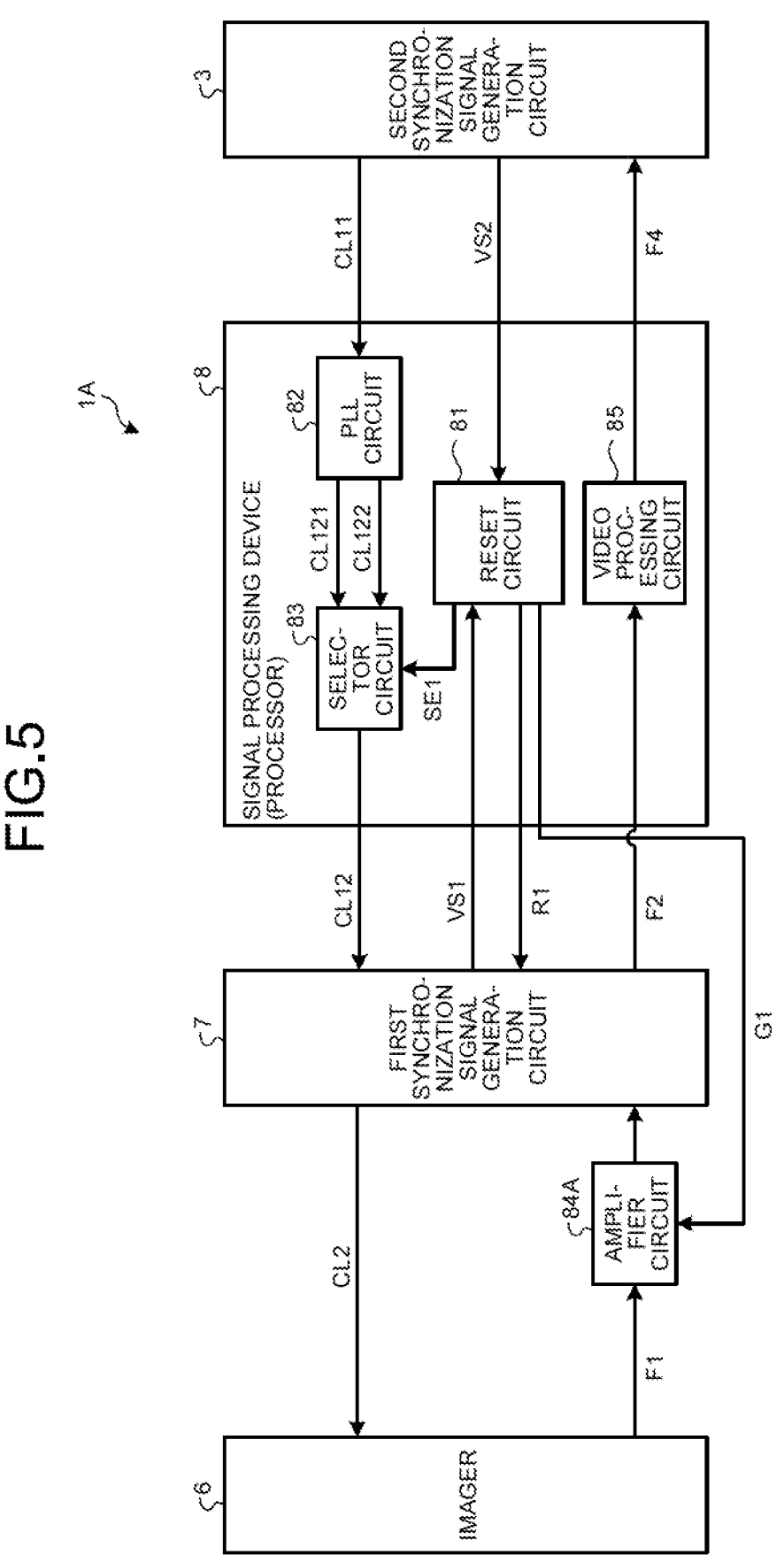
FIG. 5 is a block diagram illustrating a configuration of a main part of an endoscope system according to a second embodiment.

FIG. 5 is a diagram corresponding to FIG. 2 and is a block diagram illustrating a configuration of a main part of an endoscope system 1A according to the second embodiment.

In the endoscope system 1A according to the second embodiment, as illustrated in FIG. 5, the amplifier circuit 84 provided in the signal processing device 8 is omitted from the endoscope system 1 (FIG. 2) described in the above-described first embodiment. Then, in the endoscope system 1A, an amplifier circuit 84A having the same function as the amplifier circuit 84 is provided. The amplifier circuit 84 is provided on a line between the imager 6 and the first synchronization signal generation circuit 7, and an image signal is transmitted on the line. That is, the amplifier circuit 84A amplifies the image signal F1 output from the imager 6 with the first gain during a period in which it receives the low-level gain signal G1 from the reset circuit 81. The amplifier circuit 84 outputs the amplified image signal F1 to first synchronization signal generation circuit 7. On the other hand, the amplifier circuit 84A amplifies the image signal F1 with a second gain larger than the first gain during a period in which it receives the high-level gain signal G1 from the reset circuit 81. The amplifier circuit 84 outputs the amplified image signal F1 to first synchronization signal generation circuit 7.

The second embodiment described above has the following effects in addition to the same effects as the first embodiment described above.

Meanwhile, since the first synchronization signal generation circuit 7 converts an analog signal into a digital signal, the image signal F1 is an analog signal, and the image signal F2 is a digital signal.

By amplifying the image signal F1 that is an analog signal, it is possible to display an image in which contrast between color and brightness is maintained as compared with a case where the image signal F2 that is a digital signal is amplified.

Third Embodiment

Next, the third embodiment will be described.

In the following description, the same reference numerals are given to the same configurations as those of the above-described first embodiment, and detailed configurations thereof are omitted or simplified.

Figure 6:
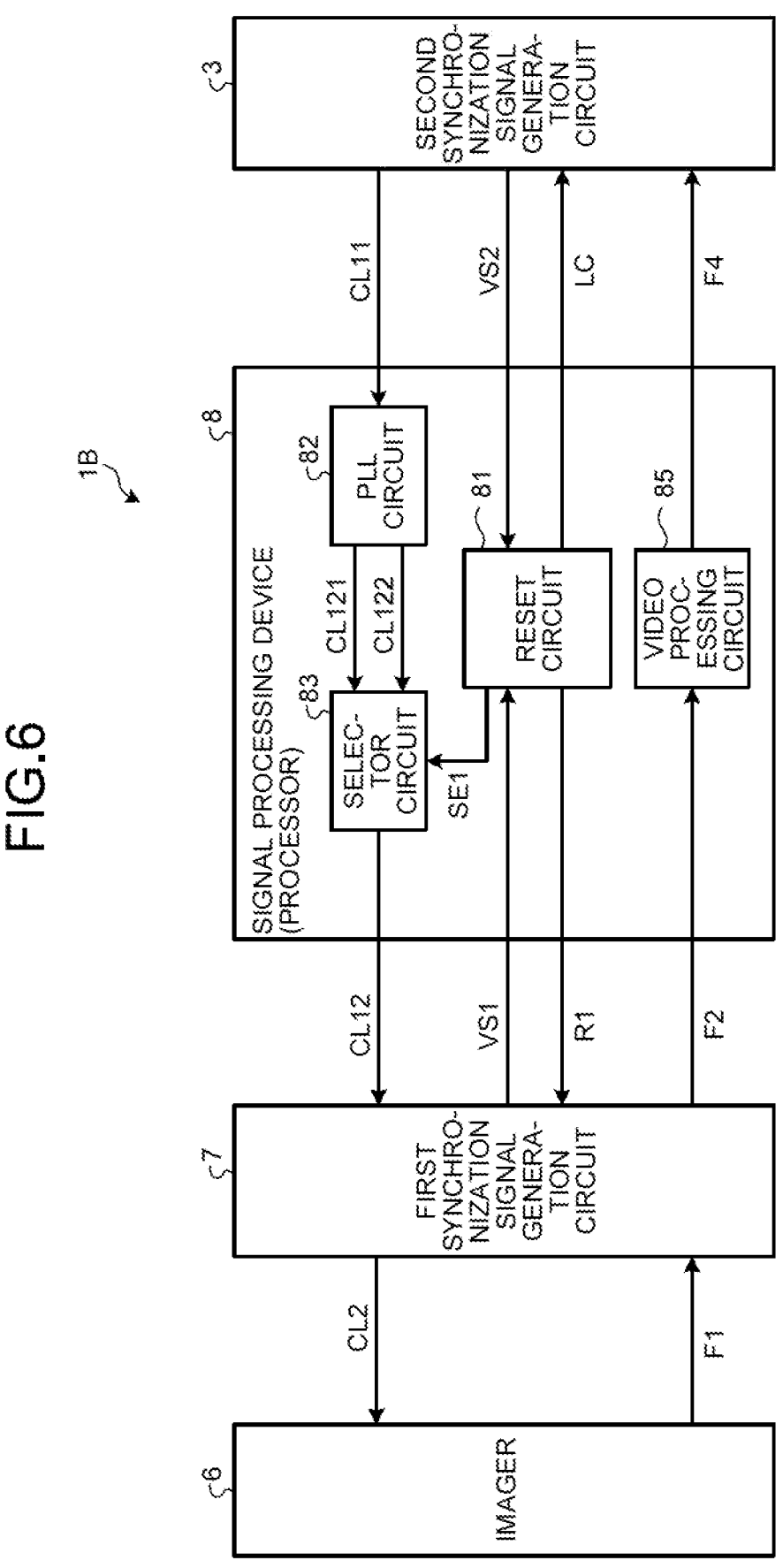
FIG. 6 is a block diagram illustrating a configuration of a main part of an endoscope system according to a third embodiment.
Figure 7:
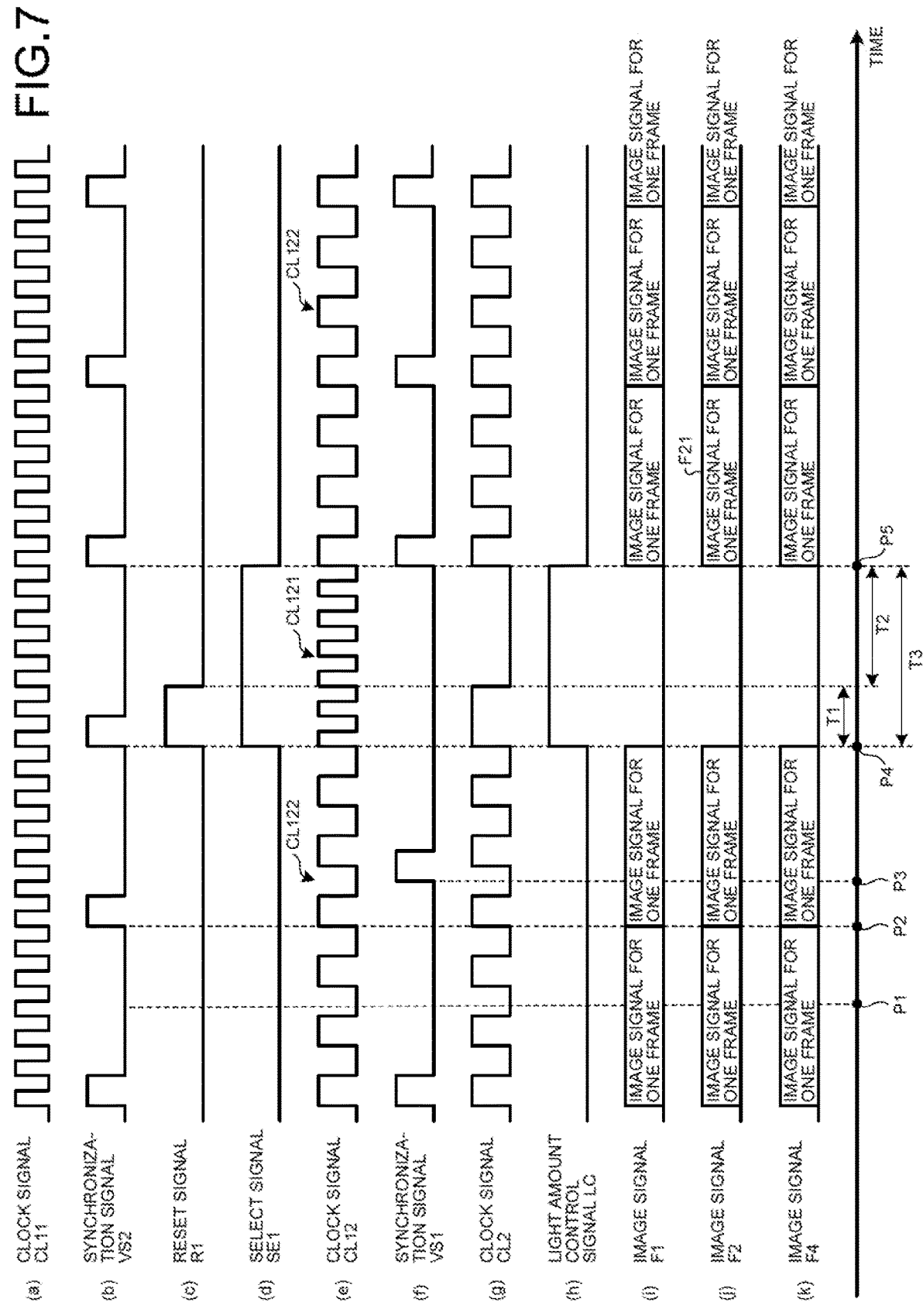
FIG. 7 is a time chart illustrating an operation of the endoscope system.

FIG. 6 is a diagram corresponding to FIG. 2 and is a block diagram illustrating a configuration of a main part of an endoscope system 1B according to the third embodiment. FIG. 7 is a time chart corresponding to that in FIG. 3, and is a time chart illustrating the operation of the endoscope system 1B. Specifically, (a) to (k) in FIG. 7 illustrate the clock signal CL11, the synchronization signal VS2, the reset signal R1, the select signal SE1, the clock signal CL12, the synchronization signal VS1, the light amount control signal LC, the image signal F1, the image signal F2, and the image signal F4, respectively.

In the endoscope system 1B according to the third embodiment, as illustrated in FIG. 6, the amplifier circuit 84 provided in the signal processing device 8 is omitted from the endoscope system 1 (FIG. 2) described in the above-described first embodiment. In addition, the reset circuit 81 outputs a high-level light amount control signal LC to the second synchronization signal generation circuit 3 in the period T3 in which the first synchronization signal generation circuit 7 is reset ((h) in FIG. 6). In a period other than the period T3, the reset circuit 81 outputs a low-level light amount control signal LC to the second synchronization signal generation circuit 3. Then, the second synchronization signal generation circuit 3 controls the operation of the light source device 5 during the period T3 in which it receives the high-level light amount control signal LC, and sets an amount of light of the illumination light emitted from the light source device 5 in the period T3 to be higher than that in another period.

According to the third embodiment described above, the following effects are obtained in addition to the same effects as those of the first embodiment described above.

In the endoscope system 1B according to the third embodiment, the amount of illumination light in the period T3 is set to be higher than that in another period. That is, since the amount of light of the illumination light is increased even during the period T2 in which a period during which charges can be accumulated is short, it is possible to brighten the image based on the image signal F21 for one frame input to the signal processing device 8 during the period T4 and display an appropriate image.

In addition, since it is not necessary to amplify the image signal, it is possible to brighten the image based on the image signal F21 and display an appropriate image without amplifying noise.

Other Embodiments

Although the embodiments for carrying out the disclosure have been described so far, the disclosure should not be limited only by the above-described first to third embodiments.

In the above-described first to third embodiments, the reset circuit 81 determines whether the synchronization signal VS1 and the synchronization signal VS2 are synchronized, and resets the first synchronization signal generation circuit 7 when determining that the synchronization signal VS1 and the synchronization signal VS2 are not synchronized. However, the reset circuit 81 may not execute the determination.

For example, in a case where a user such as an operator determines that an appropriate image is not displayed on the display device 4, the user performs an operation on an input unit (not illustrated) constituting the endoscope systems 1, 1A, and 1B. Then, the reset circuit 81 resets the first synchronization signal generation circuit 7 according to the operation.

That is, the function of determining whether the synchronization signal VS1 and the synchronization signal VS2 are synchronized may be removed from the reset circuit 81 (signal processing device 8).

In the above-described first to third embodiments, the signal processing device 8 is configured separately from the second synchronization signal generation circuit 3, but the disclosure is not limited thereto, and it may be mounted in the second synchronization signal generation circuit 3. Similarly, the signal processing device 8 is configured separately from the first synchronization signal generation circuit 7, but the disclosure is not limited thereto, and it may be mounted in the first synchronization signal generation circuit 7.

According to the signal processing device, the signal processing method, and the endoscope system according to the disclosure, it is possible to display an appropriate image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A signal processing device comprising
a processor comprising at least one or more pieces of hardware, the processor being configured to:
when a first synchronization signal output from a first synchronization signal generation circuit and a second synchronization signal output from a second synchronization signal generation circuit are synchronized, output a second clock signal to the first synchronization signal generation circuit to output the first synchronization signal, based on a first clock signal input from the second synchronization signal generation circuit,
when the first synchronization signal output from the first synchronization signal generation circuit and the second synchronization signal output from the second synchronization signal generation circuit are not synchronized, reset the first synchronization signal generation circuit, and
output a third clock signal to the first synchronization signal generation circuit to output the first synchronization signal, based on the first clock signal input from the second synchronization signal generation circuit, wherein the third clock signal has a higher frequency than the second clock signal.

2. The signal processing device according to claim 1, wherein
the processor is further configured to
determine whether the first synchronization signal and the second synchronization signal are synchronized, and
reset the first synchronization signal generation circuit when it is determined that the first synchronization signal and the second synchronization signal are not synchronized.

3. The signal processing device according to claim 2, wherein
the processor is further configured to
determine that the first synchronization signal and the second synchronization signal are not synchronized when a pulse based on the first synchronization signal and a pulse based on the second synchronization signal rise at different times.

4. The signal processing device according to claim 1, wherein
the processor is further configured to
brighten an image based on an image signal for at least one frame output from an imager after the first synchronization signal generation circuit is reset.

5. The signal processing device according to claim 4, wherein
the processor is further configured to
multiply the image signal by a gain that is a larger one of two gains to be multiplied to the image signal.

6. The signal processing device according to claim 5, wherein
the processor is further configured to
multiply an image signal output from the first synchronization signal generation circuit by the larger one of the two gains.

7. The signal processing device according to claim 5, wherein
the processor is further configured to
multiply an image signal output from the imager and input to the first synchronization signal generation circuit by the larger one of the two gains.

8. The signal processing device according to claim 1, wherein
the processor is further configured to
generate two clock signals, and
in a period in which the first synchronization signal generation circuit is reset, input to the first synchronization signal generation circuit, a clock signal having a higher frequency of the two clock signals as the first clock signal.

9. The signal processing device according to claim 1, further comprising
a phase locked loop circuit, and
a selector circuit configured to select one of clock signals, wherein
the phase locked loop circuit is configured to generate the second clock signal and the third clock signal based on the first clock signal output from the second synchronization signal generation circuit, and
the selector circuit is configured to select and output the third clock signal to the first synchronization signal generation circuit in a period in which the first synchronization signal generation circuit is reset.

10. The signal processing device according to claim 1, wherein
a period from when the first synchronization signal generation circuit starts resetting to when the resetting is completed is shorter than a period after the first synchronization signal generation circuit is reset until an image signal for one frame is output from an imager.

11. The signal processing device according to claim 1, wherein
a period from when the first synchronization signal generation circuit starts resetting to when the resetting is completed is a vertical synchronization period based on the second synchronization signal.

12. The signal processing device according to claim 1, wherein
in a period in which the first synchronization signal generation circuit is reset, the frequency of the third clock signal is set to twice a frequency of the second clock signal.

13. An endoscope system comprising:
an endoscope configured to be inserted into a subject, the endoscope including a first synchronization signal generation circuit and an imager configured to performing imaging operation based on a first synchronization signal output from the first synchronization signal generation circuit; and
a processor comprising at least one or more pieces of hardware, the processor including a second synchronization signal generation circuit, the processor being configured to:
when the first synchronization signal output from the first synchronization signal generation circuit and a second synchronization signal output from the second synchronization signal generation circuit are synchronized, output a second clock signal to the first synchronization signal generation circuit to output the first synchronization signal, based on a first clock signal input from the second synchronization signal generation circuit,
when the first synchronization signal output from the first synchronization signal generation circuit and the second synchronization signal output from the second synchronization signal generation circuit are not synchronized, reset the first synchronization signal generation circuit, and output a third clock signal to the first synchronization signal generation circuit to output the first synchronization signal, based on the first clock signal input from the second synchronization signal generation circuit, wherein the third clock signal has a higher frequency than the second clock signal.

14. The endoscope system according to claim 13, further comprising:

a light source configured to emit illumination light with which the subject is irradiated, wherein the processor is further configured to in the period in which the first synchronization signal generation circuit is reset, control an operation of the light source to set an amount of light of the illumination light in the period to be higher than an amount of light in another period.

15. The endoscope system according to claim 13, wherein the processor further includes a phase locked loop circuit, and a selector circuit configured to select one of clock signals, the phase locked loop circuit is configured to generate the second clock signal and the third clock signal based on the first clock signal output from the second synchronization signal generation circuit, and the selector circuit is configured to select and output the third clock signal to the first synchronization signal generation circuit in a period in which the first synchronization signal generation circuit is reset.

16. The endoscope system according to claim 13, wherein a period from when the first synchronization signal generation circuit starts resetting to when the resetting is completed is shorter than a period after the first synchronization signal generation circuit is reset until an image signal for one frame is output from the imager.

17. The endoscope system according to claim 13, wherein a period from when the first synchronization signal generation circuit starts resetting to when the resetting is completed is a vertical synchronization period based on the second synchronization signal.

18. The endoscope system according to claim 13, wherein in a period in which the first synchronization signal generation circuit is reset, the frequency of the third clock signal is set to twice a frequency of the second clock signal.

* * * * *